(12) United States Patent
Luttrull et al.

(10) Patent No.: US 9,381,116 B2
(45) Date of Patent: *Jul. 5, 2016

(54) SUBTHRESHOLD MICROPULSE LASER PROPHYLACTIC TREATMENT FOR CHRONIC PROGRESSIVE RETINAL DISEASES

(71) Applicant: Ojai Retinal Technology, LLC, Ojai, CA (US)

(72) Inventors: Jeffrey K. Luttrull, Ojai, CA (US); Benjamin W. L. Margolis, Oakland, CA (US); David B. Chang, Tustin, CA (US)

(73) Assignee: Ojai Retinal Technology, LLC, Ojai, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/921,890

(22) Filed: Oct. 23, 2015

(65) Prior Publication Data
US 2016/0058617 A1  Mar. 3, 2016

Related U.S. Application Data

(63) Continuation-in-part of application No. 14/607,959, filed on Jan. 28, 2015, now Pat. No. 9,168,174, which is a continuation-in-part of application No. 13/798,523, filed on Mar. 13, 2013, and a continuation-in-part of application No. 13/481,124, filed on May 25, 2012.

(51) Int. Cl.
*A61B 18/20* (2006.01)
*A61F 9/008* (2006.01)
*A61B 19/00* (2006.01)

(52) U.S. Cl.
CPC ......... *A61F 9/00821* (2013.01); *A61B 19/5212* (2013.01); *A61F 9/008* (2013.01); *A61F 9/00817* (2013.01); *A61F 2009/00863* (2013.01)

(58) Field of Classification Search
CPC . A61F 9/00821; A61F 9/008; A61F 9/00817; A61F 2009/00863; A61B 19/5212; A61N 5/06; A61N 5/1017; A61N 2005/0648
USPC .............................................. 606/4; 128/898
See application file for complete search history.

(56) References Cited

U.S. PATENT DOCUMENTS

| 3,408,593 | A | 10/1968 | Hurwitz, Jr. |
| 4,048,011 | A | 9/1977 | Kovin et al. |

(Continued)

FOREIGN PATENT DOCUMENTS

| WO | 2006005038 A2 | 1/2006 |
| WO | 2007035855 A2 | 3/2007 |
| WO | 2007106521 A2 | 9/2007 |

OTHER PUBLICATIONS

International Search Report for PCT/US2015/060836 mailing date Jan. 29, 2016.

(Continued)

*Primary Examiner* — Aaron Roane
(74) *Attorney, Agent, or Firm* — Kelly & Kelley, LLP

(57) ABSTRACT

A process for treating an eye to stop or delay the onset or symptoms of retinal diseases includes determining that the eye has a risk for a retinal disease before detectable retinal imaging abnormalities. A laser light beam is generated that provides preventative and protective treatment of the retinal tissue of the eye. At least a portion of the retinal tissue is exposed to the laser light beam without damaging the tissue. The retina may be retreated according to a set schedule or periodically according to the determination that the retina of the patient is to be retreated by monitored visual and/or retinal function or condition.

20 Claims, 8 Drawing Sheets

(56) References Cited

U.S. PATENT DOCUMENTS

| | | | |
|---|---|---|---|
| 4,176,325 A | 11/1979 | Kajimura et al. |
| 4,194,114 A | 3/1980 | Pankratov et al. |
| 4,410,365 A | 10/1983 | Glukhovsky et al. |
| 4,695,733 A | 9/1987 | Pesavento |
| 4,730,335 A | 3/1988 | Clark et al. |
| 4,791,634 A | 12/1988 | Miyake |
| 4,865,029 A | 9/1989 | Pankratov et al. |
| 4,879,722 A | 11/1989 | Dixon et al. |
| 4,930,504 A | 6/1990 | Diamantopoulos et al. |
| 4,933,944 A | 6/1990 | McGraw |
| 4,935,931 A | 6/1990 | McGraw |
| 4,961,079 A | 10/1990 | Owens et al. |
| 4,967,416 A | 10/1990 | Esterowitz et al. |
| 5,037,421 A | 8/1991 | Boutacoff et al. |
| 5,067,951 A | 11/1991 | Greve |
| 5,085,492 A | 2/1992 | Kelsoe et al. |
| 5,088,803 A | 2/1992 | Buzawa |
| 5,147,354 A | 9/1992 | Boutacoff et al. |
| 5,372,595 A | 12/1994 | Gaasterland et al. |
| 5,394,199 A | 2/1995 | Flower |
| 5,430,756 A | 7/1995 | Hanihara |
| 5,520,680 A | 5/1996 | Shapshay et al. |
| 5,651,019 A | 7/1997 | Goldberg et al. |
| 5,982,789 A | 11/1999 | Marshall et al. |
| 6,066,128 A | 5/2000 | Bahmanyar et al. |
| 6,208,769 B1 | 3/2001 | Pankratov |
| 6,222,869 B1 | 4/2001 | Marshall et al. |
| 6,327,291 B1 | 12/2001 | Marshall |
| 6,377,599 B1 | 4/2002 | Marshall |
| 6,540,391 B2 | 4/2003 | Lanzetta et al. |
| 6,681,185 B1 | 1/2004 | Young et al. |
| 6,715,877 B2 | 4/2004 | Molebny |
| 6,733,490 B1 | 5/2004 | Falsini et al. |
| 6,813,942 B1 | 11/2004 | Vozhdaev et al. |
| 6,889,695 B2 | 5/2005 | Pankratov et al. |
| 7,227,196 B2 | 6/2007 | Burgener, II et al. |
| 7,387,785 B1 | 6/2008 | Rudin et al. |
| 7,452,081 B2 | 11/2008 | Wiltberger et al. |
| 7,645,276 B2 | 1/2010 | Pankratov et al. |
| 7,763,828 B2 | 7/2010 | Talwar et al. |
| 7,766,903 B2 | 8/2010 | Blumenkranz et al. |
| 7,766,904 B2 | 8/2010 | McGowan, Sr. et al. |
| 7,771,417 B2 | 8/2010 | Telfair et al. |
| 7,909,816 B2 | 3/2011 | Buzawa |
| 2002/0120255 A1 | 8/2002 | Sotiropoulos et al. |
| 2005/0069531 A1 | 3/2005 | Karageozian et al. |
| 2005/0176662 A1 | 8/2005 | Inana et al. |
| 2008/0015553 A1 | 1/2008 | Zacharias |
| 2010/0152716 A1 | 6/2010 | Previn et al. |
| 2010/0168724 A1 | 7/2010 | Sramek et al. |
| 2010/0249760 A1 | 9/2010 | Blumenkranz et al. |
| 2010/0290007 A1 | 11/2010 | Van de Velde |
| 2011/0196350 A1 | 8/2011 | Friedman et al. |
| 2013/0317570 A1 | 11/2013 | Luttrull et al. |

OTHER PUBLICATIONS

Yeow, J.T.W. et al.; Micromachined 2-D scanner for 3-D optical coherence tomography; Sensors and Actuators A: Physical, vol. 117, Issue 2, Jan. 14, 2005, pp. 331-340; Elsevier.

Luttrull, JK et al.; Subthreshold diode micropulse panretinal photocoagulation for proliferative diabetic retinopathy Eye (2007), 1-6; Eye advance online publication Jan. 16, 2009.

Luttrull, J K et al.; Subthreshold diode micropulse photocoagulation for the treatment of clinically significant diabetic macular oedema; Br J Ophthalmol 2005; 89:74-80.

Luttrull, Jeffrey K., MD et al.; Serial Optical Coherence Tomography of Subthreshold Diode Laser Micropulse Photocoagulation for Diabetic Macular Edema; Ophthalmic Surgery, Lasers & Imaging; Sep./Oct. 2006; vol. 37, No. 5; pp. 370-377.

Luttrull, J K et al.; Subthreshold diode micropulse photocoagulation for the treatment of clinically significant diabetic macular oedema; Eye (2009) Macmillan Publishers Limited 2009.

Small Beam Diameter Scanning Galvo Mirror Systems; Thorlabs; 1999-2013, 4 pgs.

Keller, Matthew D. et al.; Raman Spectroscopy for Cancer Diagnosis; www.spectroscopyonline.com; Nov. 2006 21(11); pp. 33-41 (including Reference (21) thereof).

SUBTHRESHOLD MICROPULSE LASER PROPHYLACTIC TREATMENT FOR CHRONIC PROGRESSIVE RETINAL DISEASES

RELATED APPLICATION

This application is a continuation-in-part of U.S. application Ser. No. 14/607,959, filed Jan. 28, 2015, which is a continuation-in-part of U.S. application Ser. No. 13/798,523, filed Mar. 13, 2013; and is also a continuation-in-part of U.S. application Ser. No. 13/481,124, filed May 25, 2012.

BACKGROUND OF THE INVENTION

The present invention generally relates to phototherapy or photostimulation of biological tissue, such as laser retinal photocoagulation therapy. More particularly, the present invention is directed to a process for treating an eye to stop or delay the onset of symptoms of retinal diseases in a patient using harmless, subthreshold phototherapy or photostimulation of the retina.

The complications of chronic progressive retinal diseases, such as diabetic retinopathy (DR) and age-related macular degeneration (AMD) constitute major causes of visual loss worldwide. Complications of diabetic retinopathy remain a leading cause of vision loss in people under sixty years of age. Diabetic macular edema is the most common cause of legal blindness in this patient group. Diabetes mellitus, the cause of diabetic retinopathy, and thus diabetic macular edema, is increasing in incidence and prevalence worldwide, becoming epidemic not only in the developed world, but in the developing world as well. Diabetic retinopathy may begin to appear in persons with Type I (insulin-dependent) diabetes within three to five years of disease onset. The prevalence of diabetic retinopathy increases with duration of disease. By ten years, 14%-25% of patients will have diabetic macular edema. By twenty years, nearly 100% will have some degree of diabetic retinopathy. Untreated, patients with clinically significant diabetic macular edema have a 32% three-year risk of potentially disabling moderate visual loss.

General laser treatment of the retina for various disorders has been employed for over fifty years. Traditionally, laser photocoagulation characterized by intentional laser-induced thermal destruction and scarification of the retina has been employed. Photocoagulation has been found to be an effective means of producing retinal scars, and has become the technical standard for macular photocoagulation for diabetic macular edema. Due to the clinical effectiveness of retinal laser photocoagulation, the long-held view in medicine was that the beneficial effects of treatment were due to the retinal damage created by photocoagulation.

There are different exposure thresholds for retinal lesions that are haemorrhagic, ophthalmoscopically apparent, or angiographically demonstrable. A "threshold" lesion is one that is barely visible ophthalmoscopically at treatment time, a "subthreshold" lesion is one that is not visible at treatment time, and "suprathreshold" laser therapy is retinal photocoagulation performed to a readily visible endpoint. Traditional retinal photocoagulation treatment requires a visible endpoint either to produce a "threshold" lesion or a "suprathreshold" lesion so as to be readily visible and tracked. In fact, it has been believed that actual tissue damage and scarring are necessary in order to create the benefits of the procedure. The gray to white retinal burns testify to the thermal retinal destruction inherent in conventional threshold and suprathreshold photocoagulation.

With reference now to FIG. 1, a diagrammatic view of an eye, generally referred to by the reference number 10, is shown. When using phototherapy, the laser light is passed through the patient's cornea 12, pupil 14, and lens 16 and directed onto the retina 18. The retina 18 is a thin tissue layer which captures light and transforms it into the electrical signals for the brain. It has many blood vessels, such as those referred to by reference number 20, to nourish it. Various retinal diseases and disorders, and particularly vascular retinal diseases such as diabetic retinopathy, are treated using conventional thermal retinal photocoagulation, as discussed above. The fovea/macula region, referred to by the reference number 22 in FIG. 1, is a portion of the eye used for color vision and fine detail vision. The fovea is at the center of the macula, where the concentration of the cells needed for central vision is the highest. Although it is this area where diseases such as age-related macular degeneration are so damaging, this is the area where conventional photocoagulation phototherapy cannot be used as damaging the cells in the foveal area can significantly damage the patient's vision. Thus, with current convention photocoagulation therapies, the foveal region is avoided.

Until the advent of thermal retinal photocoagulation, there was generally no effective treatment for diabetic retinopathy. Using photocoagulation to produce photothermal retinal burns as a therapeutic maneuver was prompted by the observation that the complications of diabetic retinopathy were often less severe in eyes with preexisting retinal scarring from other causes. The Early Treatment of Diabetic Retinopathy Study demonstrated the efficacy of argon laser macular photocoagulation in the treatment of diabetic macular edema. Full-thickness retinal laser burns in the areas of retinal pathology were created, visible at the time of treatment as white or gray retinal lesions ("suprathreshold" retinal photocoagulation). With time, these lesions developed into focal areas of chorioretinal scarring and progressive atrophy.

With visible endpoint photocoagulation, laser light absorption heats pigmented tissues at the laser site. Heat conduction spreads this temperature increase from the retinal pigment epithelium and choroid to overlying non-pigmented and adjacent unexposed tissues. Laser lesions become visible immediately when damaged neural retina overlying the laser sight loses its transparency and scatters white ophthalmoscopic light back towards the observer.

Conventional thinking assumes that the physician must intentionally create retinal damage as a prerequisite to therapeutically effective treatment. With reference to FIG. 2, FIGS. 2A-2F are graphic representations of the effective surface area of various modes of retinal laser treatment for retinal vascular disease. The gray background represents the retina 30 which is unaffected by the laser treatment. The black areas 32 are areas of the retina which are destroyed by conventional laser techniques. The lighter gray or white areas 34 represent the areas of the retina affected by the laser, but not destroyed.

FIG. 2A illustrates the therapeutic effect of conventional argon laser retinal photocoagulation. The therapeutic effects attributed to laser-induced thermal retinal destruction include reduced metabolic demand, debulking of diseased retina, increased intraocular oxygen tension and ultra production of vasoactive cytokines, including vascular endothelial growth factor (VEGF).

With reference to FIG. 2B, increasing the burn intensity of the traditional laser burn is shown. It will be seen that the burned and damaged tissue area 32 is larger, which has resulted in a larger "halo effect" of heated, but undamaged, surrounding tissue 34. Laboratory studies have shown that increased burn intensity is associated with an enhanced therapeutic effect, but hampered by increased loss of functional retina inflammation. However, with reference to FIG. 2C, when the intensity of the conventional argon laser photocoagulation is reduced, the area of the retina 34 affected by the laser but not destroyed is also reduced, which may explain the inferior clinical results from lower-intensity/lower-density or "mild" argon laser grid photocoagulation compared to higher-intensity/higher-density treatment, as illustrated in FIG. 2B.

With reference to FIG. 2D, it has been found that low-fluence photocoagulation with short-pulse continuous wave laser photocoagulation, also known as selective retinal therapy, produces minimal optical and lateral spread of laser photothermal tissue effects, to the extent that the area of the retina affected by the laser but not destroyed is minimal to nonexistent. Thus, despite complete oblation of the directly treated retina 30, the rim of the therapeutically affected and surviving tissue is scant or absent. This explains the recent reports finding superiority of conventional argon laser photocoagulation over PASCAL for diabetic retinopathy.

That iatrogenic retinal damage is necessary for effective laser treatment of retinal vascular disease has been universally accepted for almost five decades, and remains the prevailing notion. Although providing a clear advantage compared to no treatment, current retinal photocoagulation treatments, which produce visible gray to white retinal burns and scarring, have disadvantages and drawbacks. Conventional photocoagulation is often painful. Local anesthesia, with its own attendant risks, may be required. Alternatively, treatment may be divided into stages over an extended period of time to minimize treatment pain and post-operative inflammation. Transient reduction in visual acuity is common following conventional photocoagulation.

In fact, thermal tissue damage may be the sole source of the many potential complications of conventional photocoagulation which may lead to immediate and late visual loss. Such complications include inadvertent foveal burns, pre- and subretinal fibrosis, choroidal neovascularization, and progressive expansion of laser scars. Inflammation resulting from the tissue destruction may cause or exacerbate macular edema, induced precipitous contraction of fibrovascular proliferation with retinal detachment and vitreous hemorrhage, and cause uveitis, serous choroidal detachment, angle closure or hypotony. Some of these complications are rare, while others, including treatment pain, progressive scar expansion, visual field loss, transient visual loss and decreased night vision are so common as to be accepted as inevitable side-effects of conventional laser retinal photocoagulation. In fact, due to the retinal damage inherent in conventional photocoagulation treatment, it has been limited in density and in proximity to the fovea, where the most visually disabling diabetic macular edema occurs.

Notwithstanding the risks and drawbacks, retinal photocoagulation treatment, typically using a visible laser light, is the current standard of care for proliferative diabetic retinopathy, as well as other retinopathy and retinal diseases, including diabetic macular edema and retinal venous occlusive diseases which also respond well to retinal photocoagulation treatment. In fact, retinal photocoagulation is the current standard of care for many retinal diseases, including diabetic retinopathy.

Currently, retinal imaging and visual acuity testing guide management of the detected retinal diseases. As end-organ structural damage and vision loss are late disease manifestations, treatment instituted at this point must be intensive, often prolonged and expensive, frequently failing to improve visual acuity, and rarely restoring normal vision.

Another problem is that the treatment requires the application of a large number of laser doses to the retina, which can be tedious and time-consuming. Typically, such treatments call for the application of each dose in the form of a laser beam spot applied to the target tissue for a predetermined amount of time, from a few hundred milliseconds to several seconds. Typically, the laser spots range from 50-500 microns in diameter. Their laser wavelength may be green, yellow, red or even infrared. It is not uncommon for hundreds or even in excess of one thousand laser spots to be necessary in order to fully treat the retina. The physician is responsible for insuring that each laser beam spot is properly positioned away from sensitive areas of the eye, such as the fovea, that could result in permanent damage. Laying down a uniform pattern is difficult and the pattern is typically more random than geometric in distribution. Point-by-point treatment of a large number of locations tends to be a lengthy procedure, which frequently results in physician fatigue and patient discomfort.

Accordingly, there is a continuing need for a process for treating an eye to stop or delay the onset or symptoms of retinal diseases in a patient without many of the drawbacks and complications resulting from conventional photocoagulation treatments. There is also a continuing need for a process for such treatment before retinal imaging abnormalities are detectable. Furthermore, there is a continuing need for a process that provides the application of a large number of laser doses to the treatment area, or even the entire retina, in a simultaneous manner without damaging the retinal tissue. The present invention fulfills these needs, and provides other related advantages.

SUMMARY OF THE INVENTION

The present invention is directed to a process for treating an eye to stop or delay the onset or symptoms of retinal diseases in a patient. The process generally comprises the steps of determining that an eye has a risk for a retinal disease before detectable retinal imaging abnormalities. A laser light beam is generated that creates sublethal, true subthreshold photocoagulation in retinal tissue that provides preventative and protective treatment of the retinal tissue of the eye.

The treated retina may comprise the fovea, foveola, retinal pigment epithelium, choroid, choroidal neovascular membrane, subretinal fluid, macula, macular edema, parafovea, and/or perifovea. The laser light beam may be exposed to substantially the entire retina and fovea.

Determining that an eye of the patient has a risk for a retinal disease before detectable retinal imaging abnormalities may include the step of ascertaining that the patient is at risk for a chronic progressive retinopathy, including diabetes, a risk for age-related macular degeneration or retinitis pigmentosa, or results of a retinal examination or retinal test of the patient is abnormal. A test may be conducted to establish that the patient has a risk for a retinal disease. The test may comprise a retinal physiology test or a genetic test.

The laser light beam may be generated as a subthreshold sublethal micropulse laser light beam having a wavelength greater than 532 nm and a duty cycle of less than 10%. In one embodiment, the generated laser light beam has a duty cycle of approximately 5% or less. The generated laser light beam may have a wavelength between 550 nm and 1300 nm. In one embodiment, the generated laser light beam has a wavelength of approximately 810 nm. The generated laser light beam may have an intensity of between 100-590 watts per square centimeter at a treatment spot on the retina. The generated laser light beam has a pulse length of less than 500 milliseconds.

The laser light beam may be manipulated into a geometric object or pattern of simultaneously generated and spaced apart treatment laser light spots with each spot having the intensity cited in paragraph 22. The manipulated laser light beam may comprise the step of creating a predetermined number of simultaneously generated laser light spots to completely and confluently cover a desired treatment area. The geometric object or pattern of laser light spots may cover substantially the entire retina. Alternatively, the geometric object or pattern of laser light spots may be controllably moved to treat adjacent retinal tissue. The moving step may include the step of incrementally moving the laser light beam geometric object or pattern a sufficient distance from where the laser light beam geometric object or pattern was previously applied to the retina to preclude thermal tissue damage.

The retina may be retreated periodically. The retreating of the retina may be according to a set schedule. Additionally, or alternatively, visual and/or retinal function or condition of the patient is monitored to determine when the retina of the patient is to be retreated.

Other features and advantages of the present invention will become apparent from the following more detailed description, taken in conjunction with the accompanying drawings, which illustrate, by way of example, the principles of the invention.

BRIEF DESCRIPTION OF THE PREFERRED EMBODIMENTS

The accompanying drawings illustrate the invention. In such drawings.

DETAILED DESCRIPTION OF THE PREFERRED EMBODIMENTS

As shown in the accompanying drawings, for purposes of illustration, the present invention is directed to a therapeutic process for treating an eye to stop or delay the onset or symptoms of retinal diseases, including chronic progressive retinal diseases, such as diabetic retinopathy (DR) and age-related macular degeneration (AMD).

Figure 1:
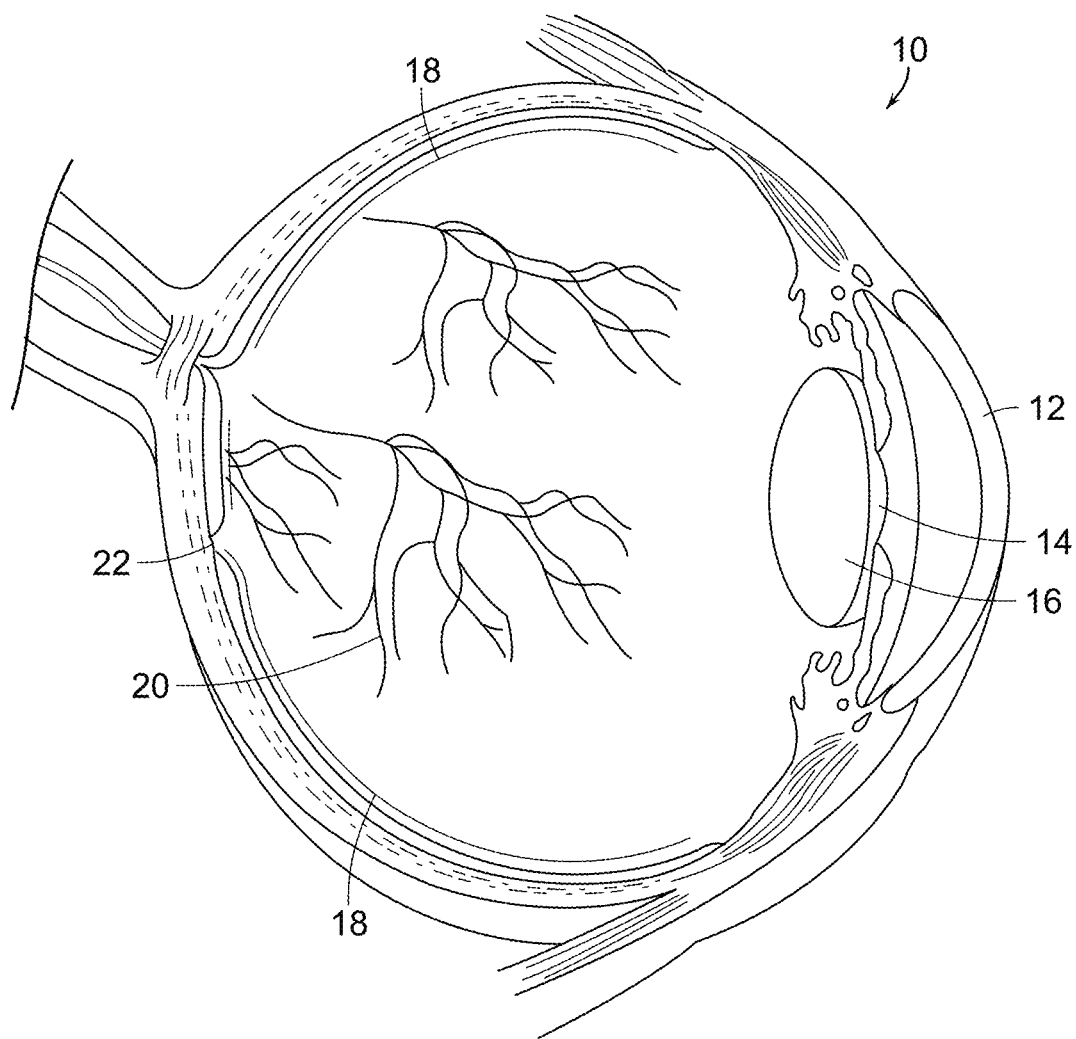
FIG. 1 is a cross-sectional diagrammatic view of a human eye.
Figure 2A:
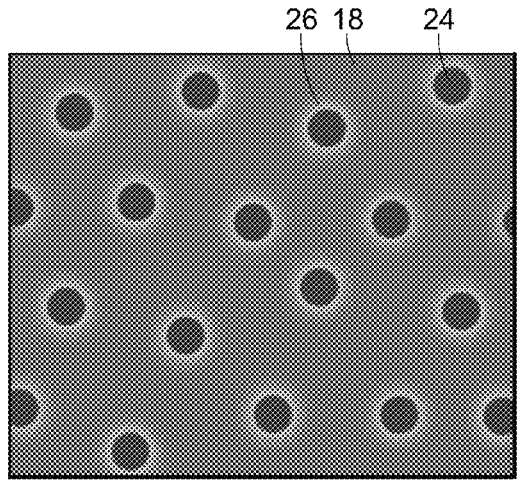
FIGS. 2A-2D are graphic representations of an effective surface area of various modes of retinal laser treatment performed in accordance with the prior art.
Figure 2B:
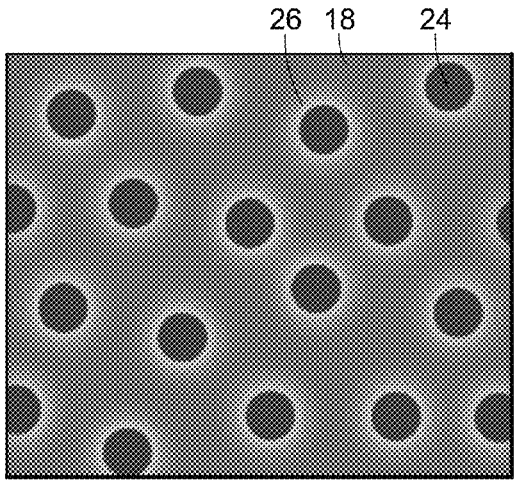
Figure 2C:
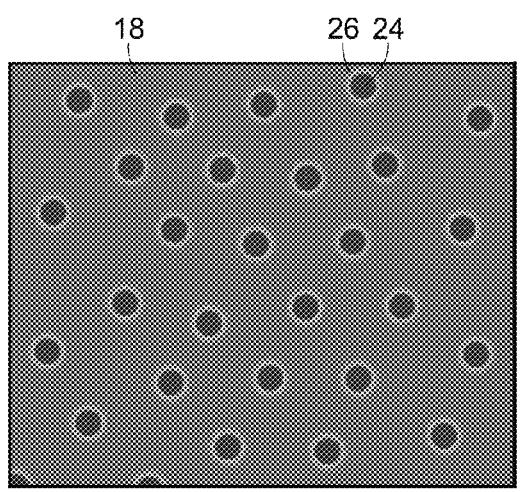
Figure 2D:
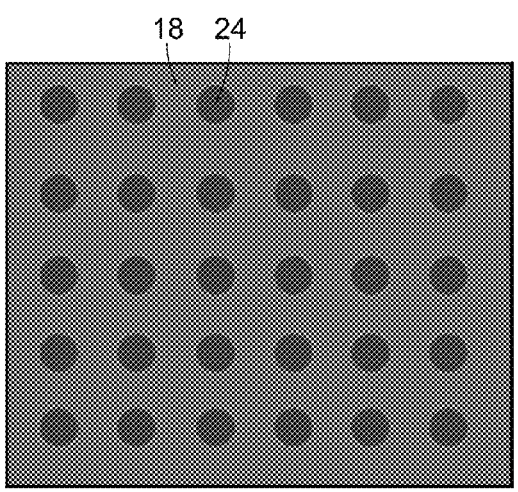

As discussed above, it is conventional thinking that tissue damage and lesions must be created by retinal laser therapy in order to have a therapeutic effect. However, the inventors have found that this simply not the case and have shown that such thermal retinal damage is unnecessary and have questioned whether it accounts for the benefits of the conventional laser treatments. The inventors have found that the therapeutic alterations in the retinal pigment epithelium (RPE) cytokine production elicited by conventional photocoagulation comes from cells at the margins of traditional laser burns, effected but not killed by the laser exposure, referred to by the reference number 26 in FIGS. 2A-2C.

The inventors have found that a laser light beam can be generated that is therapeutic, yet sublethal to retinal tissue cells and thus creates "true subthreshold" photocoagulation in the retinal tissue which provides preventative and protective treatment of the retinal tissue of the eye. The inventors have discovered that generating a subthreshold, sublethal micropulse laser light beam which has a wavelength greater than 532 nm and a duty cycle of less than 10% at a predetermined intensity or power and a predetermined pulse length or exposure time creates desirable retinal photocoagulation, shown by the reference number 28 in FIGS. 3A and 3B, without any visible burn areas or tissue destruction. More particularly, a laser light beam having a wavelength of between 550 nm-1300 nm, and in a particularly preferred embodiment 810 nm, having a duty cycle of approximately 5% or less and a predetermined intensity or power (such as between 100-590 watts per square centimeter for each treatment spot at the retina) and a predetermined pulse length or exposure time (such as 500 milliseconds or less) creates a sublethal, "true subthreshold" retinal photocoagulation in which all areas of the retinal pigment epithelium exposed to the laser irradiation are preserved and available to contribute therapeutically. In other words, the inventors have found that raising the retinal tissue at least up to a therapeutic level but below a cellular or tissue lethal level recreates the benefit of the halo effect (referred to by the reference number 26 in FIGS. 2A-2C) without destroying, burning or otherwise damaging the retinal tissue. This is referred to herein as subthreshold diode micropulse laser treatment (SDM).

Figure 3A:
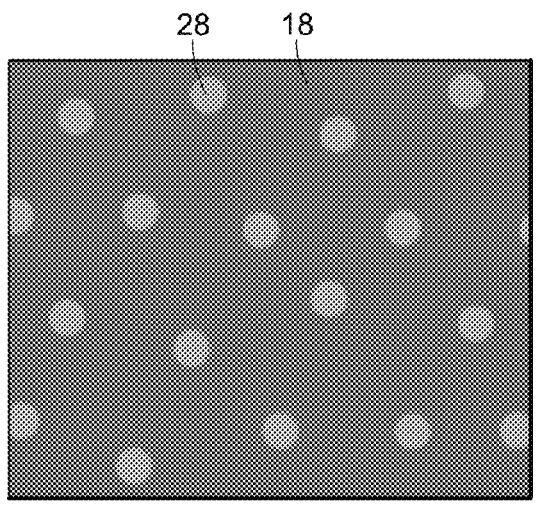
FIGS. 3A and 3B are graphic representations of effective surface areas of retinal laser treatment, in accordance with the present invention.
Figure 3B:
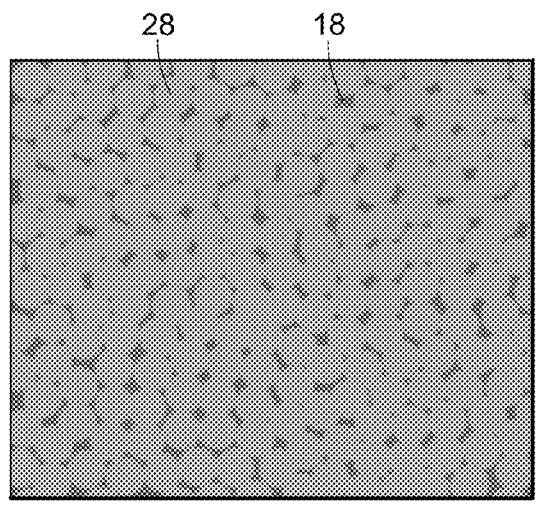

FIG. 3A represents a low-density treatment of the sublethal, "true subthreshold" SDM or low-intensity laser, such as a micropulsed laser, spots applied to retinal tissue 18 to create sublethal, subthreshold retinal photostimulation, shown by the reference number 28, without any visible burn areas. As SDM does not produce laser-induced retinal damage (photocoagulation), and has no known adverse treatment effect, and has been reported to be an effective treatment in a number of retinal disorders (including diabetic macular edema (DME) proliferative diabetic retinopathy (PDR), macular edema due to branch retinal vein occlusion (BRVO), and central serous chorioretinopathy (CSR) the present invention can be performed in a high-density manner, as illustrated in FIG. 3B so as to essentially cover the entire treatment area, and even the entire retina, including the fovea. Traditional and conventional laser photocoagulation treatment is unable to treat the entire retina, including the fovea, as the inherent burns and damage caused by the treatment can impair the vision of the patient or even cause blindness.

By definition, SDM does not cause tissue damage and has no known adverse treatment effect. SDM has been reported to be an effective treatment in a number of retinal disorders, including DME, proliferative diabetic retinopathy (PDR), macular edema due to branch retinal vein occlusion (BRVO), and central serous chorioretinopathy (CSR). The safety of SDM is such that it may be used transfoveally in eyes with 20/20 visual acuity to reduce the risk of visual loss due to early fovea-involving DME. It is believed that SDM works by targeting, preserving, and normalizing—moving toward normal—function of the RPE.

Another mechanism through which SDM might work is the generation of heat shock proteins (HSPs). Despite a near infinite variety of possible cellular abnormalities, cells of all types share a common and highly conserved mechanism of repair: heat shock proteins (HSPs). HSPs are elicited almost immediately, in seconds to minutes, by almost any type of cell stress or injury. In the absence of lethal cell injury, HSPs are extremely effective at repairing and returning the viable cell toward a more normal functional state. Although HSPs are transient, generally peaking in hours and persisting for a few days, their effects may be long lasting. HSPs reduce inflammation, a common factor in many retinal disorders, including diabetic retinopathy (DR) and AMD.

Laser treatment induces HSP production and, in the case of retinal treatment, alters retinal cytokine expression. The more sudden and severe the non-lethal cellular stress (such as laser irradiation), the more rapid and robust HSP production. Thus, a burst of repetitive low temperature thermal spikes at a very steep rate of change (~20° C. elevation with each 100 µs micropulse, or 20,000° C./sec) produced by each SDM exposure is especially effective in stimulating production of HSPs, particularly compared to non-lethal exposure to subthreshold treatment with continuous wave lasers, which can duplicate only the low average tissue temperature rise.

Laser wavelengths below 550 nm produce increasingly cytotoxic photochemical effects. At 810 nm, SDM produces photothermal, rather than photochemical, cellular stress. Thus, SDM is able to affect the tissue, including RPE, without damaging it. Consistent with HSP activation, SDM produces prompt clinical effects, such as rapid and significant improvement in retinal electrophysiology, visual acuity, contrast visual acuity and improved macular sensitivity measured by microperimetry, as well as long-term effects, such as reduction of DME and involution of retinal neovascularization.

In the retina, the clinical benefits of SDM are thus produced by sub-morbid photothermal RPE HSP activation. In dysfunctional RPE cells, HSP stimulation by SDM results in normalized cytokine expression, and consequently improved retinal structure and function. The therapeutic effects of this "low-intensity" laser/tissue interaction are then amplified by "high-density" laser application, recruiting all the dysfunctional RPE in the targeted area, thereby maximizing the treatment effect. These principles define the treatment strategy of SDM described herein. The ability of SDM to produce therapeutic effects similar to both drugs and photocoagulation indicates that laser-induced retinal damage (for effects other than cautery) is unnecessary and non-therapeutic; and, in fact, detrimental because of the loss of retinal function and incitement of inflammation.

Because normally functioning cells are not in need of repair, HSP stimulation in normal cells would tend to have no notable clinical effect. The "patho-selectivity" of near infrared laser effects, such as SDM, affecting sick cells but not affecting normal ones, on various cell types is consistent with clinical observations of SDM. This facility is key to the suitability of SDM for early and preventative treatment of eyes with chronic progressive disease and eyes with minimal retinal abnormality and minimal dysfunction. Finally, SDM has been reported to have a clinically broad therapeutic range, unique among retinal laser modalities, consistent with American National Standards Institute "Maximum Permissible Exposure" predictions. While SDM may cause direct photothermal effects such as entropic protein unfolding and disaggregation, SDM appears optimized for clinically safe and effective stimulation of HSP-mediated retinal repair.

As noted above, while SDM stimulation of RPE HSPs is non-specific with regard to the disease process, the result of HSP mediated repair is by its nature specific to the state of the dysfunction. HSPs tend to fix what is wrong, whatever that might be. Thus, the observed effectiveness of SDM in retinal conditions as widely disparate as BRVO, DME, PDR, CSR, and drug-tolerant NAMD. Conceptually, this facility can be considered a sort of "Reset to Default" mode of SDM action. For the wide range of retinal disorders in which RPE function is critical, SDM normalizes RPE function by triggering a "reset" (to the "factory default settings") via HSP-mediated cellular repair. Certainly, SDM has limitations. For instance, clinical experience with this theory suggests that SDM is less effective once RPE mediated disease-related anatomic derangement, such as in chronic cystoid macular edema, retinal atrophy and scarring, or the pathologic environment, is so severe and/or degenerative that the retina can no longer respond to RPE autoregulatory influences. That absence of sufficient viable target RPE due to severe pigmentary atrophy may preclude a treatment response.

The inventors have found that SDM treatment of patients suffering from age-related macular degeneration (AMD) can slow the progress or even stop the progression of AMD. Most of the patients have seen significant improvement in dynamic functional logMAR visual acuity and contrast visual acuity after the SDM treatment, with some experiencing better vision. It is believed that SDM works by targeting, preserving, and "normalizing" (moving toward normal) function of the retinal pigment epithelium (RPE).

SDM has also been shown to stop or reverse the manifestations of the diabetic retinopathy disease state without treatment-associated damage or adverse effects, despite the persistence of systemic diabetes mellitus. On this basis it is hypothesized that SDM might work by inducing a return to more normal cell function and cytokine expression in diabetes-affected RPE cells, analogous to hitting the "reset" button of an electronic device to restore the factory default settings.

Based on the above information and studies, SDM treatment may directly affect cytokine expression and heat shock protein (HSP) activation in the targeted tissue, particularly the retinal pigment epithelium (RPE) layer. Panretinal and panmacular SDM has been noted by the inventors to reduce the rate of progression of many retinal diseases, including severe non-proliferative and proliferative diabetic retinopathy, AMD, DME, etc. The known therapeutic treatment benefits of individuals having these retinal diseases, coupled with the absence of known SDM adverse treatment effects, allows for consideration of early and preventative treatment, liberal application and retreatment as necessary. The reset theory also suggests that SDM may have application to many different types of RPE-mediated retinal disorders. In fact, the inventor has recently shown that panmacular SDM can significantly improve retinal function and health, retinal sensitivity, and dynamic logMAR visual acuity and contrast visual acuity in dry age-related macular degeneration, retinitis pigmentosa, cone-rod retinal degenerations, and Stargardt's disease where no other treatment has previously been found to do so.

Currently, retinal imaging and visual acuity testing guide management of chronic, progressive retinal diseases. As tissue and/or organ structural damage and vision loss are late disease manifestations, treatment instituted at this point must be intensive, often prolonged and expensive, and frequently fails to improve visual acuity and rarely restores normal vision. As SDM has been shown to be an effective treatment for a number of retinal disorders without adverse treatment effects, and by virtue of its safety and effectiveness, SDM can also be used to treat an eye to stop or delay the onset or symptoms of retinal diseases prophylactically or as a preventative treatment for such retinal diseases. Any treatment that improves retinal function, and thus health, should also reduce disease severity, progression, untoward events and visual loss. By beginning treatment early, prior to pathologic structural change, and maintaining the treatment benefit by regular functionally-guided re-treatment, structural degeneration and visual loss might thus be delayed if not prevented. Even modest early reductions in the rate of disease progression may lead to significant long-term reductions and complications in visual loss. By mitigating the consequences of the primary defect, the course of disease may be muted, progression slowed, and complications and visual loss reduced.

In accordance with the present invention, it is determined that a patient, and more particularly an eye of the patient, has a risk for a retinal disease. This may be before retinal imaging abnormalities are detectable. Such a determination may be accomplished by ascertaining if the patient is at risk for a chronic progressive retinopathy, including diabetes, a risk for age-related macular degeneration or retinitis pigmentosa. Alternatively, or additionally, results of a retinal examination or retinal test of the patient may be abnormal. A specific test, such as a retinal physiology test or a genetic test, may be conducted to establish that the patient has a risk for a retinal disease.

An SDM laser light beam, that is sublethal and creates true subthreshold photocoagulation and retinal tissue, is generated and at least a portion of the retinal tissue is exposed to the generated laser light beam without damaging the exposed retinal or foveal tissue, so as to provide preventative and protective treatment of the retinal tissue of the eye. The treated retina may comprise the fovea, foveola, retinal pigment epithelium, choroid, choroidal neovascular membrane, subretinal fluid, macula, macular edema, parafovea, and/or perifovea. The laser light beam may be exposed to only a portion of the retina, or substantially the entire retina and fovea.

While most SDM effects appear to be long-lasting, if not permanent, clinical observations suggest that SDM can appear to wear off on occasion. Accordingly, the retina is periodically retreated. This may be done according to a set schedule or when it is determined that the retina of the patient is to be retreated, such as by periodically monitoring visual and/or retinal function or condition of the patient.

Figure 4:
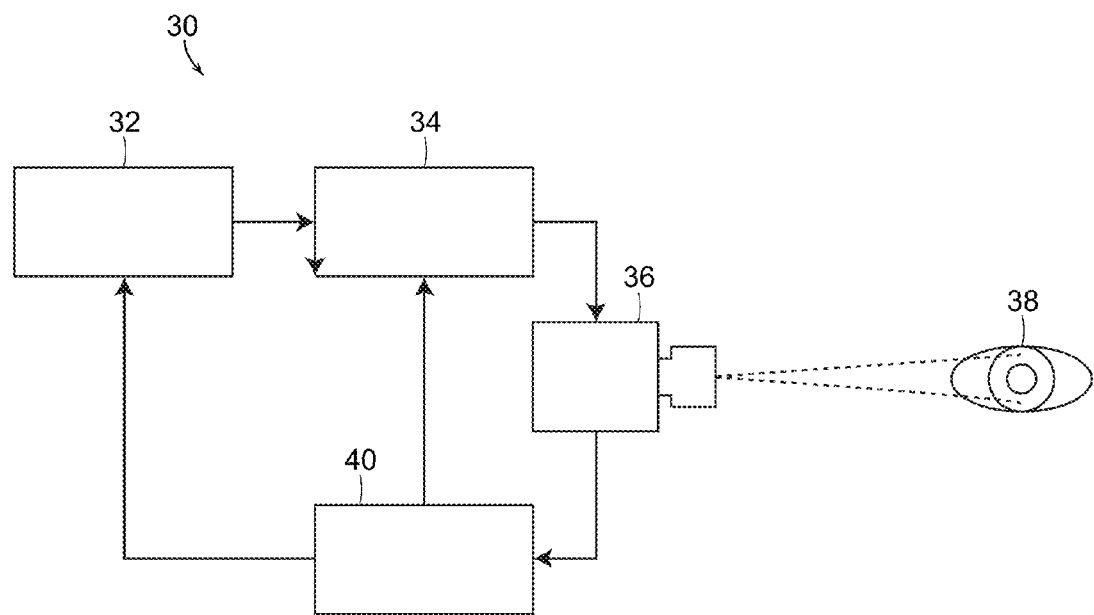
FIG. 4 is a diagrammatic view illustrating a system used to generate a laser light beam and treat an eye, in accordance with the present invention.

With reference now to FIG. 4, a schematic diagram is shown of a system for realizing the process of the present invention. The system, generally referred to by the reference number 30, includes a laser console 32, such as for example the 810 nm near infrared micropulsed diode laser in the preferred embodiment. The laser generates a laser light beam which is passed through optics, such as an optical lens or mask, or a plurality of optical lenses and/or masks 34 as needed. The laser projector optics 34 pass the shaped light beam to a coaxial wide-field non-contact digital optical viewing system/camera 36 for projecting the laser beam light onto the eye 38 of the patient. It will be understood that the box labeled 36 can represent both the laser beam projector as well as a viewing system/camera, which might in reality comprise two different components in use. The viewing system/camera 36 provides feedback to a display monitor 40, which may also include the necessary computerized hardware, data input and controls, etc. for manipulating the laser 32, the optics 34, and/or the projection/viewing components 36.

Figure 5:
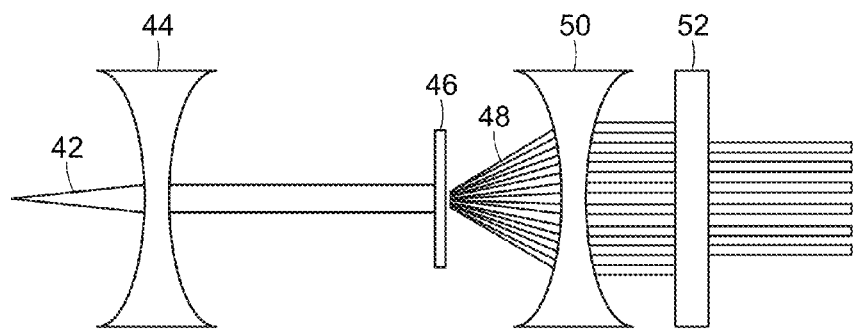
FIG. 5 is a diagrammatic view of optics used to generate a laser light geometric pattern, in accordance with the present invention.

With reference now to FIG. 5, in one embodiment, the laser light beam 42 is passed through a collimator lens 44 and then through a mask 46. In a particularly preferred embodiment, the mask 46 comprises a diffraction grating. The mask/diffraction grating 46 produces a geometric object, or more typically a geometric pattern of simultaneously produced multiple laser spots or other geometric objects. This is represented by the multiple laser light beams labeled with reference number 48. Alternatively, the multiple laser spots may be generated by a plurality of fiber optic wires. Either method of generating laser spots allows for the creation of a very large number of laser spots simultaneously over a very wide treatment field, such as consisting of the entire retina. In fact, a very high number of laser spots, perhaps numbering in the hundreds even thousands or more could cover the entire ocular fundus and entire retina, including the macula and fovea, retinal blood vessels and optic nerve. The intent of the process in the present invention is to better ensure complete and total coverage and treatment, sparing none of the retina by the laser so as to improve vision.

Using optical features with a feature size on par with the wavelength of the laser employed, for example using a diffraction grating, it is possible to take advantage of quantum mechanical effects which permits simultaneous application of a very large number of laser spots for a very large target area. The individual spots produced by such diffraction gratings are all of a similar optical geometry to the input beam, with minimal power variation for each spot. The result is a plurality of laser spots with adequate irradiance to produce harmless yet effective treatment application, simultaneously over a large target area. The present invention also contemplates the use of other geometric objects and patterns generated by other diffractive optical elements.

The laser light passing through the mask 46 diffracts, producing a periodic pattern a distance away from the mask 46, shown by the laser beams labeled 48 in FIG. 5. The single laser beam 42 has thus been formed into hundreds or even thousands of individual laser beams 48 so as to create the desired pattern of spots or other geometric objects. These laser beams 48 may be passed through additional lenses, collimators, etc. 50 and 52 in order to convey the laser beams and form the desired pattern on the patient's retina. Such additional lenses, collimators, etc. 50 and 52 can further transform and redirect the laser beams 48 as needed.

Arbitrary patterns can be constructed by controlling the shape, spacing and pattern of the optical mask 46. The pattern and exposure spots can be created and modified arbitrarily as desired according to application requirements by experts in the field of optical engineering. Photolithographic techniques, especially those developed in the field of semiconductor manufacturing, can be used to create the simultaneous geometric pattern of spots or other objects.

Figure 6:
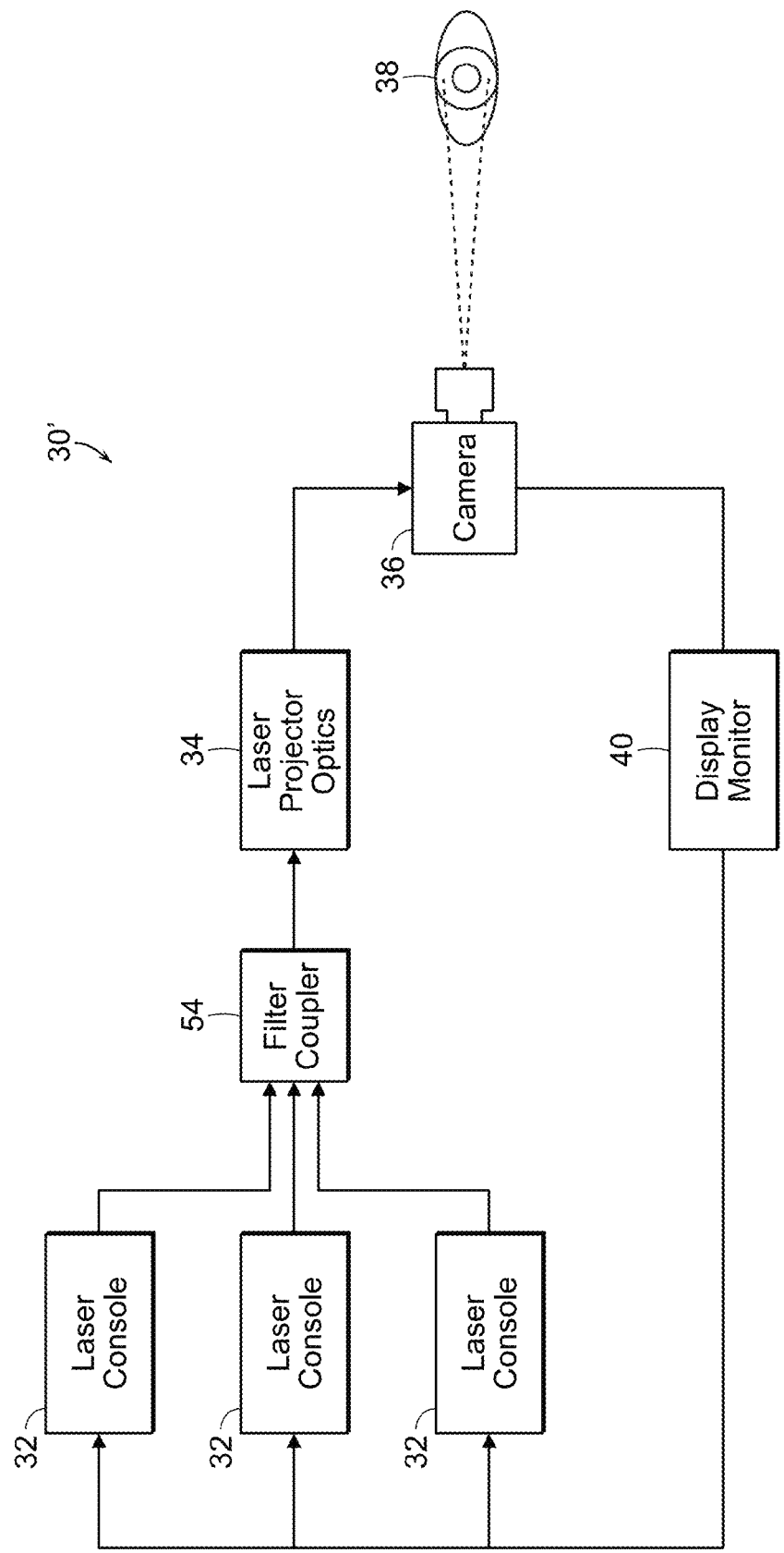
FIG. 6 is a diagrammatic view illustrating an alternate embodiment of a system used to generate laser light beams for treating an eye, in accordance with the present invention.

FIG. 6 illustrates diagrammatically a system which couples multiple light sources into the pattern-generating optical subassembly described above. Specifically, this system 30' is similar to the system 30 described in FIG. 4 above. The primary differences between the alternate system 30' and the earlier described system 30 is the inclusion of a plurality of laser consoles 32, the outputs of which are each fed into a fiber coupler 54. The fiber coupler produces a single output that is passed into the laser projector optics 34 as described in the earlier system. The coupling of the plurality of laser consoles 32 into a single optical fiber is achieved with a fiber coupler 54 as is known in the art. Other known mechanisms for combining multiple light sources are available and may be used to replace the fiber coupler described herein.

In this system 30' the multiple light sources 32 follow a similar path as described in the earlier system 30, i.e., collimated, diffracted, recollimated, and directed into the retina with a steering mechanism. In this alternate system 30' the diffractive element must function differently than described earlier depending upon the wavelength of light passing through, which results in a slightly varying pattern. The variation is linear with the wavelength of the light source being diffracted. In general, the difference in the diffraction angles is small enough that the different, overlapping patterns may be directed along the same optical path through the steering mechanism 36 to the retina 38 for treatment. The slight difference in the diffraction angles will affect how the steering pattern achieves coverage of the retina.

Since the resulting pattern will vary slightly for each wavelength, a sequential offsetting to achieve complete coverage will be different for each wavelength. This sequential offsetting can be accomplished in two modes. In the first mode, all wavelengths of light are applied simultaneously without identical coverage. An offsetting steering pattern to achieve complete coverage for one of the multiple wavelengths is used. Thus, while the light of the selected wavelength achieves complete coverage of the retina, the application of the other wavelengths achieves either incomplete or overlapping coverage of the retina. The second mode sequentially applies each light source of a varying wavelength with the proper steering pattern to achieve complete coverage of the retina for that particular wavelength. This mode excludes the possibility of simultaneous treatment using multiple wavelengths, but allows the optical method to achieve identical coverage for each wavelength. This avoids either incomplete or overlapping coverage for any of the optical wavelengths.

These modes may also be mixed and matched. For example, two wavelengths may be applied simultaneously with one wavelength achieving complete coverage and the other achieving incomplete or overlapping coverage, followed by a third wavelength applied sequentially and achieving complete coverage.

Figure 7:
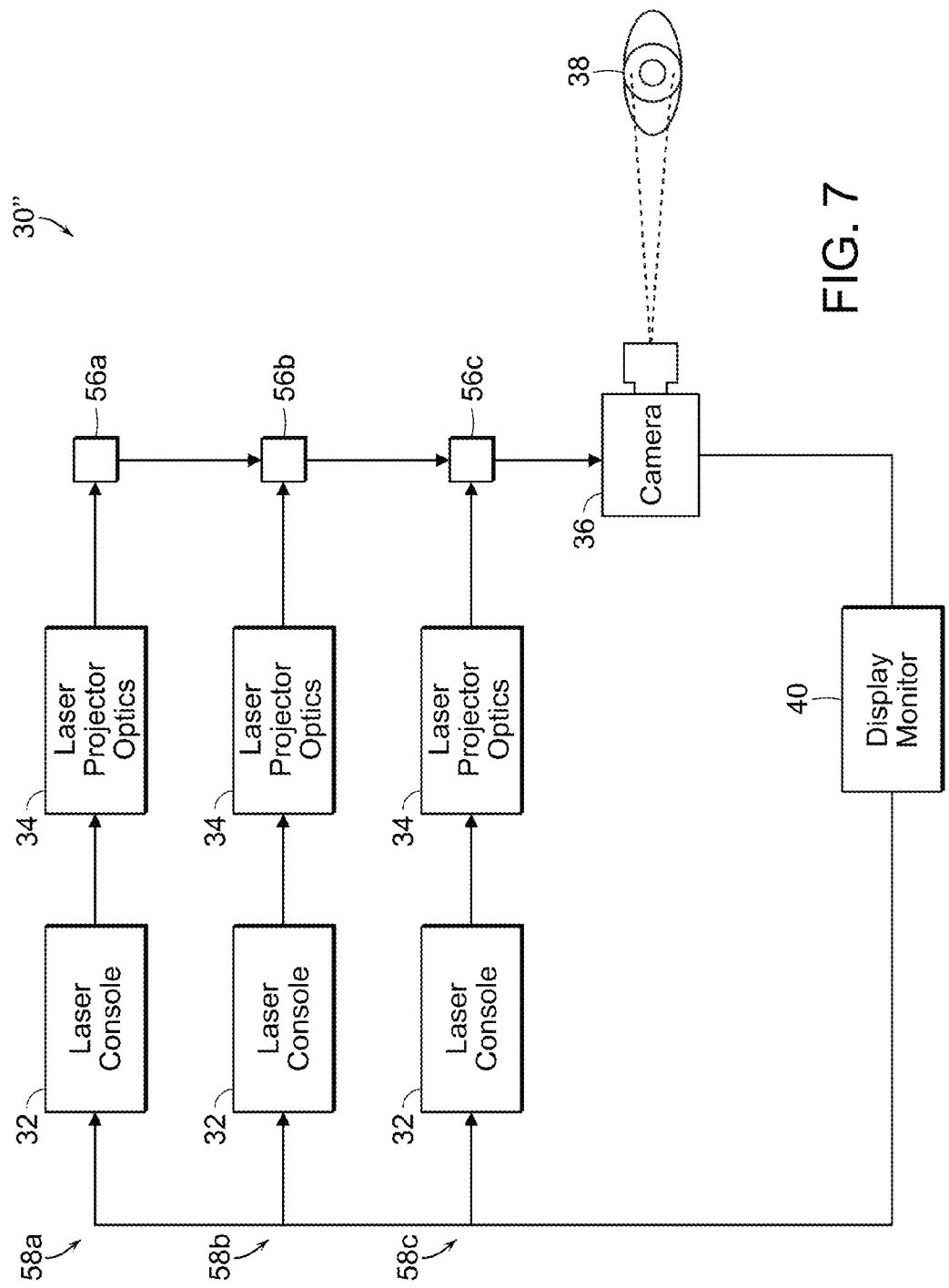
FIG. 7 is a diagrammatic view illustrating yet another embodiment of a system used to generate laser light beams to treat an eye in accordance with the present invention.

FIG. 7 illustrates diagrammatically yet another alternate embodiment of the inventive system 30". This system 30" is configured generally the same as the system 30 depicted in FIG. 4. The main difference resides in the inclusion of multiple pattern-generating subassembly channels tuned to a specific wavelength of the light source. Multiple laser consoles 32 are arranged in parallel with each one leading directly into its own laser projector optics 34. The laser projector optics of each channel 58a, 58b, 58c comprise a collimator 44, mask or diffraction grating 48 and recollimators 50, 52 as described in connection with FIG. 5 above—the entire set of optics tuned for the specific wavelength generated by the corresponding laser console 32. The output from each set of optics 34 is then directed to a beam splitter 56 for combination with the other wavelengths. It is known by those skilled in the art that a beam splitter used in reverse can be used to combine multiple beams of light into a single output.

The combined channel output from the final beam splitter 56c is then directed through the camera 36 which applies a steering mechanism to allow for complete coverage of the retina 38.

In this system 30" the optical elements for each channel are tuned to produce the exact specified pattern for that channel's wavelength. Consequently, when all channels are combined and properly aligned a single steering pattern may be used to achieve complete coverage of the retina for all wavelengths.

The system 30" may use as many channels 58a, 58b, 58c, etc. and beam splitters 56a, 56b, 56c, etc. as there are wavelengths of light being used in the treatment.

Implementation of the system 30" may take advantage of different symmetries to reduce the number of alignment constraints. For example, the proposed grid patterns are periodic in two dimensions and steered in two dimensions to achieve complete coverage. As a result, if the patterns for each channel are identical as specified, the actual pattern of each channel would not need to be aligned for the same steering pattern to achieve complete coverage for all wavelengths. Each channel would only need to be aligned optically to achieve an efficient combination.

In system 30", each channel begins with a light source 32, which could be from an optical fiber as in other embodiments of the pattern-generating subassembly. This light source 32 is directed to the optical assembly 34 for collimation, diffraction, recollimation and directed into the beam splitter which combines the channel with the main output.

Typically, the system of the present invention incorporates a guidance system to ensure complete and total retinal treatment with retinal photostimulation. As the treatment method of the present invention is harmless, the entire retina, including the fovea and even optical nerve, can be treated. Moreover, protection against accidental visual loss by accidental patient movement is not a concern. Instead, patient movement would mainly affect the guidance in tracking of the application of the laser light to ensure adequate coverage. Fixation/tracking/registration systems consisting of a fixation target, tracking mechanism, and linked to system operation are common in many ophthalmic diagnostic systems and can be incorporated into the present invention.

Figure 8:
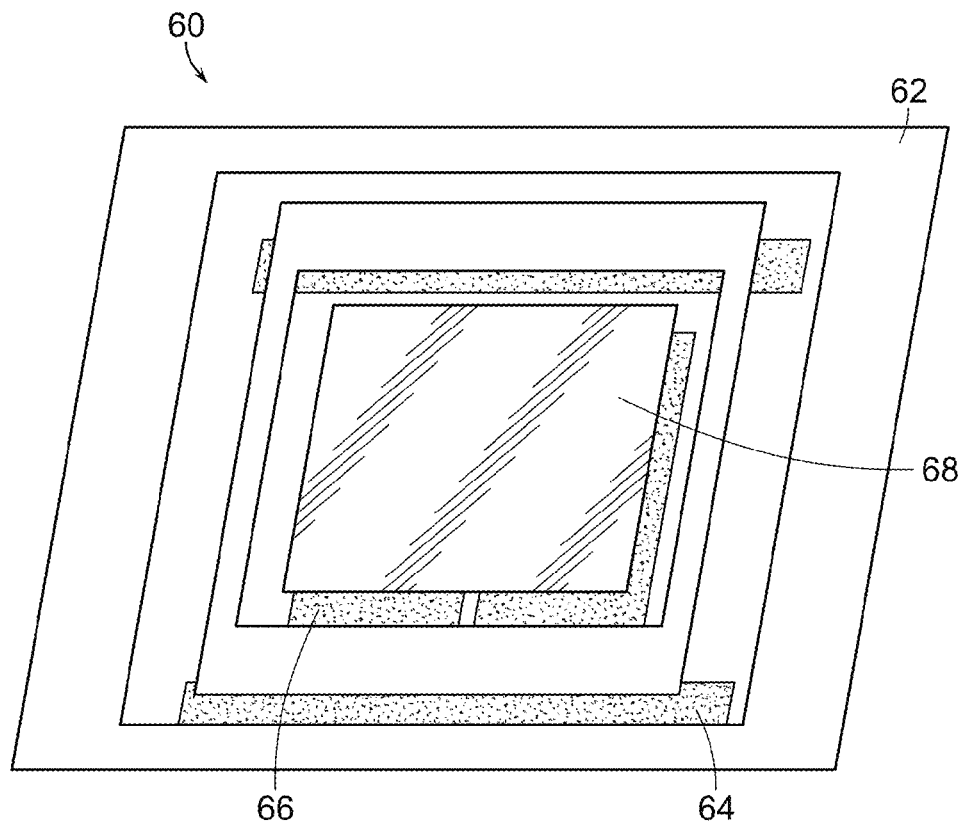
FIG. 8 is a top plan view of an optical scanning mechanism, used in accordance with the present invention.
Figure 9:
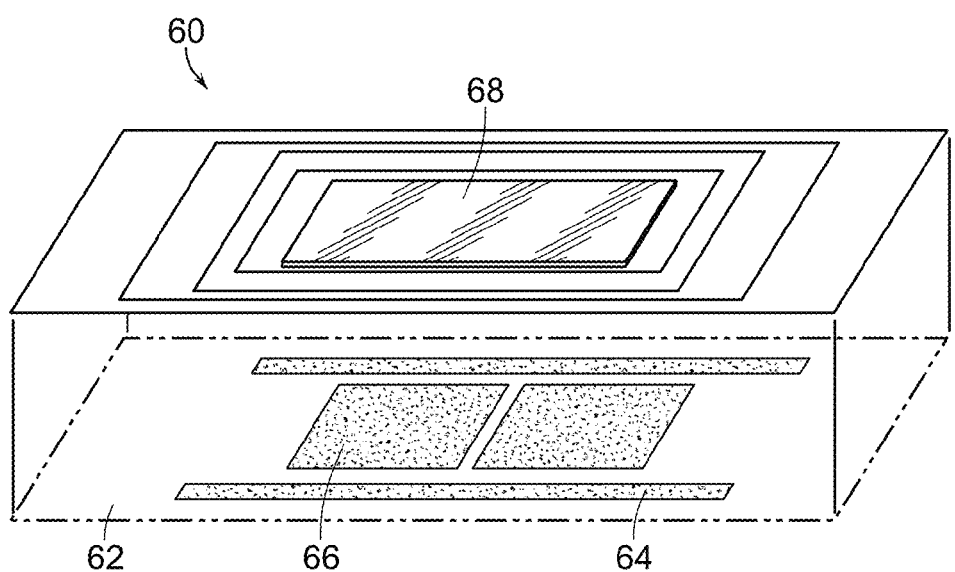
FIG. 9 is a partially exploded view of the optical scanning mechanism of FIG. 8, illustrating various component parts thereof.

With reference now to FIGS. 8 and 9, in a particularly preferred embodiment, the geometric pattern of simultaneous laser spots is sequentially offset so as to achieve confluent and complete treatment of the retinal surface. Although a segment of the retina can be treated in accordance with the present invention, more ideally the entire retina will be treated with one treatment. This is done in a time-saving manner by placing hundreds to thousands of spots over the entire ocular fundus at once. This pattern of simultaneous spots is scanned, shifted, or redirected as an entire array sequentially, so as to cover the entire retina.

This can be done in a controlled manner using an optical scanning mechanism 60. FIGS. 8 and 9 illustrate an optical scanning mechanism 60 in the form of a MEMS mirror, having a base 62 with electronically actuated controllers 64 and 66 which serve to tilt and pan the mirror 68 as electricity is applied and removed thereto. Applying electricity to the controller 64 and 66 causes the mirror 68 to move, and thus the simultaneous pattern of laser spots or other geometric objects reflected thereon to move accordingly on the retina of the patient. This can be done, for example, in an automated fashion using electronic software program to adjust the optical scanning mechanism 60 until complete coverage of the retina, or at least the portion of the retina desired to be treated, is exposed to the phototherapy. The optical scanning mechanism may also be a small beam diameter scanning galvo mirror system, or similar system, such as that distributed by Thorlabs. Such a system is capable of scanning the lasers in the desired offsetting pattern.

Figure 10:
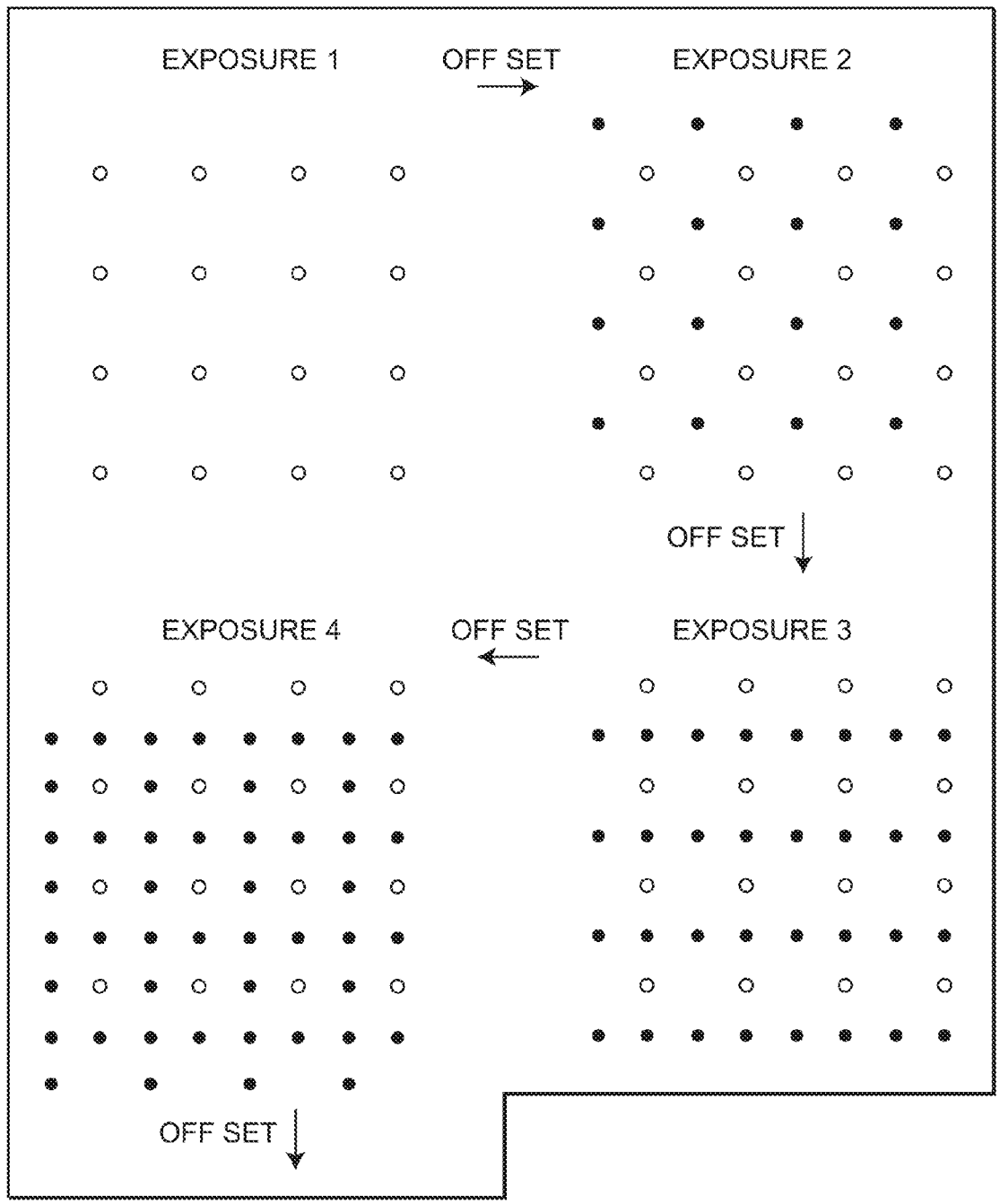
FIG. 10 is a diagrammatic view illustrating the offsetting of a geometric pattern of laser spots over multiple exposures so as to substantially cover an area of the eye being treated, in accordance with the present invention.

With reference now to FIG. 10, a diagrammatic representation of the process of sequentially offsetting laser spots is shown. A geometric pattern of laser spots is shown in an initial exposure 1, the geometric pattern is offset and the retina is exposed again in exposure 2, wherein the current exposure is shown by the circles and the prior exposure(s)

shown and represented by the solid dots. The spacing of the laser spots prevents overheating and damage to the tissue. This is repeated over multiple exposures until the entire treatment area, or even the entire retina, has been exposed to the SDM laser treatment. In this manner a low-density treatment, as illustrated in FIG. 3A, can become a high-density treatment, as illustrated in FIG. 3B. Of course, however, the optics and number of laser spots generated and the distance between laser spots could be such that an entire treatment area, or even the entire retina, could be exposed simultaneously with only a single exposure.

The invention described herein is generally safe for pan-retinal and/or trans-foveal treatment. However, it is possible that a user, i.e., surgeon, preparing to limit treatment to a particular area of the retina where disease markers are located or to prevent treatment in a particular area with darker pigmentation, such as from scar tissue.

The American Standards Institute (ANSI) has developed standards for safe workplace laser exposure based on the combination of theoretical and empirical data. The "maximum permissible exposure" (MPE) is the safety level, set at approximately $1/10^{th}$ of the laser exposure level expected to produce biological effects. At a laser exposure level of 1 times MPE, absolute safety would be expected and retinal exposure to laser radiation at this level would be expected to have no biologic affect. Based on ANSI data, a 50% of some risk of suffering a barely visible (threshold) burn is generally encountered at 10 times MPE for conventional continuous wave laser exposure. For a low-duty cycle micropulsed laser exposure of the same power, the risk of threshold burn is approximately 100 times MPE. Thus, the therapeutic range—the interval of doing nothing at all and the 50% of some likelihood of producing a threshold burn—for low-duty cycle micropulsed laser irradiation is 10 times wider than for continuous wave laser irradiation with the same energy. It has been determined that safe and effective sublethal, true subthreshold photocoagulation using a micropulsed diode laser is between 18 times and 55 times MPE, with a preferred laser exposure, for example, to retinal tissue at 47 times MPE for a near-infrared 810 nm diode laser. At this level, it has been observed that there is therapeutic effectiveness with no discernible retinal damage whatsoever.

It has been found that the intensity or power of a laser between 100 watts to 590 watts, and preferably 350 watts, per square centimeter at a retinal treatment spot is effective yet safe. A particularly preferred intensity or power of the laser light is approximately one watt per laser spot for an 810 nm micropulsed diode laser.

Power limitations in current micropulsed diode lasers require fairly long exposure duration. The longer the exposure, the more important the center-spot heat dissipating ability toward the unexposed tissue at the margins of the laser spot and toward the underlying choriocapillaris as in the retina. Thus, the micropulsed laser light beam of an 810 nm diode laser should have an exposure envelope duration of 500 milliseconds or less, and preferably approximately 300 milliseconds. Of course, if micropulsed diode lasers become more powerful, the exposure duration should be lessened accordingly.

Another parameter of the present invention is the duty cycle (the frequency of the train of micropulses, or the length of the thermal relaxation time in between consecutive pulses). It has been found that the use of a 10% duty cycle or higher adjusted to deliver micropulsed laser at similar irradiance at similar MPE levels significantly increase the risk of lethal cell injury, particularly in darker fundi. However, duty cycles less than 10%, and preferably approximately 5% duty cycle (or less, such as 2.5%) demonstrate adequate thermal rise and treatment at the level of the MPE cell to stimulate a biologic response, but remain below the level expected to produce lethal cell injury, even in darkly pigmented fundi. If the duty cycle is less than 5%, the exposure envelope duration in some instances can exceed 500 milliseconds.

In a particularly preferred embodiment, small laser spots are used. This is due to the fact that larger spots can contribute to uneven heat distribution and insufficient heat dissipation within the large laser spot, potentially causing tissue damage or even tissue destruction towards the center of the larger laser spot. In this usage, "small" would generally apply to spots less than 1 mm in diameter. However, the smaller the spot, the more ideal the heat dissipation and uniform energy application becomes. Thus, at the power intensity and exposure duration described above, small spots, such as along the size of the wavelength of the laser, or small geometric lines or other objects are preferred so as to maximize even heat distribution and heat dissipation to avoid tissue damage.

Thus, the following key parameters have been found in order to create harmless, "true" subthreshold photocoagulation in accordance with the present invention: a) a low (preferably 5% or less) duty cycle; b) a small spot size to minimize heat accumulation and assure uniform heat distribution within a given laser spot so as to maximize heat dissipation; c) sufficient power to produce laser exposures of between 18 times-55 times MPE producing a tissue temperature rise of no more than 7° C.-14° C.; and irradiance of between 100-590 W/cm².

Using the foregoing parameters, a harmless, "true" subthreshold photocoagulation phototherapy treatment can be attained which has been found to produce the benefits of conventional photocoagulation phototherapy, but avoids the drawbacks and complications of conventional phototherapy. In fact, sublethal, "true" subthreshold photocoagulation phototherapy in accordance with the present invention enables the physician to apply a "low-intensity/high-density" phototherapy treatment, for example as illustrated in FIG. 3B for treatment of the entire retina, including sensitive areas such as the macula and even the fovea without creating visual loss or other damage. As indicated above, using conventional phototherapies was impossible on the entire retina, particularly the fovea, as it would create vision loss due to the tissue damage in sensitive areas at the retina.

An analysis of the effectiveness and safety of the discussed SDM treatment has been performed with approximations to the exact equations for the laser absorption, heat diffusion, and Arrhenius reaction rates describing the process. Comparisons have also been made with the same approximate equations for alternate approaches (CW and Pascal and nanosecond CW laser exposures). The following indicates that for typical operating parameters, SDM is both safe and effective, whereas the alternate techniques can be either ineffective or not safe.

Results for Arrhenius integrals from approximate equations:

TABLE 1

Four typical laser treatments:

| Laser parameters type | Retinal spot diameter (μm) | Laser power (mW) | Exposure time (ms) | Duty Cycle (repeat rate) |
|---|---|---|---|---|
| Canonical SDM | 131 | 950 | 300 | 5% (500 Hz) |
| CW power equiv to SDM | 131 | 47.5 | 300 | 100% |

TABLE 1-continued

Four typical laser treatments:

| Laser parameters type | Retinal spot diameter (μm) | Laser power (mW) | Exposure time (ms) | Duty Cycle (repeat rate) |
|---|---|---|---|---|
| CW temps equiv to SDM | 131 | 37 | 300 | 100% |
| CSMO Pascal | 200 | 21.26 | 15 | 100% |

In the first four cases, the laser wavelength is 810 nm, while in the Pascal case, the wavelength is 532 nm. The absorption coefficient for 532 nm is approximately 4 times that for 810 nm.

The Arrhenius integral results for damage and HSP production for these four treatments are summarized in Table 2.

TABLE 2

Arrhenius integral results for the treatments of Table 1 (using our approximate equations). dTp is the temperature rise of the first pulse (and only pulse, for the 3 CW parameters). dToo' is the baseline temperature rise of the pulse train for SDM. Ω(dmg) is the arrhenius integral for damage using the Arrhenius rate parameters from the MPE data for minimum retinal radius. Ω(HSP) is the Arrhenius integral for HSP stimulation. For the 810 nm cases, an experimentally-based optical transmission efficiency of 80% has been assumed in calculating the temperature rises.

| Laser parameters type | dTp | dToo' | Ω(dmg) | Ω(HSP) |
|---|---|---|---|---|
| Canonical SDM | 8.78K | 7.30K | 0.024 | 2.01 |
| CW power equiv to SDM | 34.12K | | 22.1 | 346 |
| CW temps equiv to SDM | 7.37K | | 0.017 | 1.62 |
| CSMO Pascal | 7.13K | | 0.0012 | 0.14 |

Damage occurs when Ω(dmg) > 1, and HSP production occurs when Ω(HSP) > 1. Accordingly, the desired treatment result is for Ω(dmg) < 1 and Ω(HSP) > 1.

As Table 2 shows, only the canonical SDM treatment and the CW temperature equivalent to SDM accomplishes this.

Following such treatment with a high-density/low-intensity subthreshold diode micropulse laser there may be treatment verification and monitoring. Responses to the treatment described herein may be detectable by retinal function testing pre-therapeutically. Such tests may include pattern electroretinography (PERG), microperimetry, and threshold microvisual acuity testing, which are all existing technologies. Such post-treatment, pre-therapeutic retinal function testing allows for conformation of treatment administration and effect. It also allows one to prospectively follow patients to determine the need for retreatment, indicated by worsening results of retinal function testing. By combining retinal function testing with true-subthreshold treatment allows for a treatment modality able to demonstrate a desired immediate treatment effect absent detectable retinal damage. The retinal function testing also allows for the prevention of disease progression by detecting early on a need for re-treatment prophylactically.

Current retinal treatment measures are anatomic, meaning that they are "late"-term indicators—abnormal only in advanced and end-stage diseases. Using retinal function indicators that may improve in apparently normal eyes prior to the development of anatomic changes can help document treatment benefits in the absence of anatomic derangement. The retinal function testing can be used to signal the need for re-treatment prior to the development of anatomic disease. The ability to prevent clinical/anatomic disease, vision loss, and the need for more intensive and expensive treatments can be rationally minimized.

The process and methodology of the present invention has been the subject of an initial experimental trial study. The invention was offered as a prophylaxis/retinal protection for high-risk AMD and inherited degenerations (IRD). Testing was performed within one week prior to SDM treatment and within one month after treatment. The results of retinal and visual function testing in a group of those patients evaluated before and after SDM prophylaxis by pattern electroretinography (PERG), automated microperimetry (AMP) and central vision analyzer (CVA) testing.

PERG was performed using standard protocols of a commercially available system (Diopsys® Nova-ERG, Diopsys Corp., Pine Brook, N.J.) according to International Society for Clinical Electrophysiology of Vision standards. Both eyes were tested simultaneously and recorded individually, undilated, and refracted for a 60 cm testing distance. For all visual stimuli, a luminance pattern occupying a 25° visual field is presented with a luminance reversal rate of 15 Hz.

For IRD, a PERG "Concentric Ring" (CR) visual stimulus optimized for analyzing peripheral retinal sensitivity was employed, presenting with a circle of one luminance and an outer ring with the contrasting luminance. The concentric ring stimulus used two sub-classes of stimuli with an inner circle occupying a visual field of 16° and 24°, respectively. The concentric ring stimuli used a mean luminance of 117.6 $cd/m^2$ with a contrast of 100%.

For AMD, in addition to the CR scans, Contrast Sensitivity (CS) stimuli were employed, presenting a grid of 64×64 cells, alternating luminance levels, recording a high contrast (HC) test with a mean luminance of 112 $cd/m^2$ and a contrast of 85%, and a low contrast (LC) test with a mean luminance of 106.4 $cd/m^2$ and a contrast of 75%.

Patient and equipment preparation were carried out according to Diopsys™ guidelines. Signal acquisition and analysis followed a standard glaucoma screening protocol. Test indices available for analysis included "Magnitude D", "Magnitude (μV)", and the "MagD(μV)/Mag(μV)" ratio. "Magnitude D" [MagD(μV)] is the frequency response of the time-domain averaged signal in microvolts (μV). Macular and/or ganglion cell dysfunction cause signal latencies resulting in magnitude and phase variability that reduce MagD by phase cancelation. Magnitude (μV) [Mag(μV)] measures the frequency response of the total signal in microvolts (μV). Mag (μV) reflects the signal strength and electrode impedance of the individual test sessions, as well as a gross measure of ganglion function. The MagD(μV)/Mag(μV) ratio thus provides a measure of patient response normalized to that particular test's electrical quality. The closer MagD(μV)/Mag (μV) to unity, the more normal macular function.

AMP (MAIA, Centervue Inc, Fremont, Calif.) testing was performed without dilation or anesthesia, according to manufacturer recommendations. Data recorded included percent-reduced thresholds, average threshold, and percent primary and secondary fixation localization.

CVA (Visoptics, Mechanicsberg, Pa.) is an FDA approved measure of visual acuity. A thresholding algorithm is used to dynamically determine logMAR central visual acuity for 6 different levels of contrast, ranging from 99% to 35%, using an interactive computer interface.

Following informed consent and pupillary dilation, topical proparacaine was applied to the cornea. A Mainster macular contact lens (Ocular Instruments, Mentor, Ohio, magnification factor 1.05×) was placed on the cornea with the aid of viscoelastic. Under minimum slit-lamp illumination, the entire posterior retina circumscribed by the major vascular arcades was "painted" with 1800-3000 confluent spot applications of SDM ("panmacular" treatment). The laser parameters used were 810 nm wavelength, 200 um aerial spot size, 5% duty cycle; and 1.6 watt power and 0.075 second duration (Oculight SLx, Iris Medical/Iridex Corp, Mountain View, Calif.).

All data was anonymized prior to statistical analysis. All analyses were performed using linear mixed models predicting the measure, with an indicator for time as a covariate, adjusting for left or right eye, and including a random patient intercept to correct for possible inter-eye correlation. Finally, univariate linear mixed models, predicting the difference (post-minus pre-treatment) with pre-treatment value as covariate were performed. The coefficients and p-values from six such models were compared.

In the following, "macular function" and "retinal function" refer to the physiology and electrophysiology of the retina. In contrast, "visual function" is used to refer to measurements such as visual acuity, visual fields, and contrast sensitivity.

220 eyes of 166 patients undergoing panmacular SDM prophylaxis for high-risk AMD and IRD were identified. These included 210 eyes of 158 patients treated for AMD; and 10 eyes of 8 patients treated for IRD. Of these, 167 consecutive eyes of 108 patients with AMD, and 10 consecutive eyes of 8 patients with IRD were evaluated before and after SDM by PERG and thus eligible for study. IRD diagnoses included rod-cone degeneration (4 eyes), cone-rod degeneration (3 eyes), and Stargardt's disease (3 eyes). Visual function testing was performed in 113 consecutive AMD eyes concurrently with PERG; including AMP in 40 consecutive eyes, and CVA testing in the subsequent 73 consecutive eyes.

Overall, 149/168 eyes were improved by PERG after SDM. Snellen visual acuities, ranging from 20/20 to CF preoperatively, were unchanged. Patients with geographic atrophy frequently reported prompt subjective lightening or disappearance of their prior central scotoma. There were no adverse treatment effects.

139/158 eyes with high-risk dry AMD were improved by PERG following SDM. Post SDM CS HC MagD(uV)/Mag (uV) ratios were not significantly improved (P=0.09). However, CS LC MagD(uV)/Mag(uV) ratios (P=0.0001) and CS LC MagD(uV) amplitudes (P=0.02) were significantly improved.

TABLE 3

Comparison of various measured values (Post-minus Pre-Treatment), PERG Contrast Sensitivity Test eyes, for high-risk age-related macular degeneration in response to panmacular SDM laser retinal protective therapy.

| ,Variable | Mean (SD) | Median (IQR) | p-value |
| --- | --- | --- | --- |
| M(d)/M(uv) Ratio, High Contrast | 0.05 (0.19) | 0.04 (−0.07, 0.17) | 0.09 |
| M(d)/M(uv) Ratio, Low Contrast | 0.08 (0.17) | 0.08 (0.00, 0.17) | 0.001 |
| M(d) Measure, High Contrast | 0.05 (0.32) | 0.05 (−0.17, 0.26) | 0.37 |
| M(d) Measure, Low Contrast | 0.08 (0.25) | 0.07 (−0.06, 0.21) | 0.02 |

TABLE 3-continued

Comparison of various measured values (Post-minus Pre-Treatment), PERG Contrast Sensitivity Test eyes, for high-risk age-related macular degeneration in response to panmacular SDM laser retinal protective therapy.

| ,Variable | Mean (SD) | Median (IQR) | p-value |
| --- | --- | --- | --- |
| M(uv) Measure, High Contrast | −0.04 (0.34) | −0.04 (−0.23, 0.14) | 0.42 |
| M(uv) Measure, Low Contrast | −0.03 (0.33) | 0.01 (−0.19, 0.17) | 0.55 |

Table 3 shows the comparisons of interest for the PERG Contrast Sensitivity Test dataset. Each row shows the difference (post-minus pre-treatment) in M(d)/M(uv) ratio, M(d) measure, or M(uv) measure, at the two contrast options. In order to test whether the mean difference is different from zero, linear mixed models predicting the measure, using an indicator for time as a covariate, also adjusting for left or right eye, and including a random patient intercept, were performed. The p-values are those associated with the time (pre-versus post-) regression coefficient. A significant p-value indicates that the mean difference is significantly different from zero. The table shows that M(d)/M(uv) ratio, low contrast, as well as M(d) measure, low contrast, are significantly higher post-treatment compared to pre-treatment (positive values indicate higher post-treatment values, negative values indicate higher pre-treatment values). This method accounts for inter-eye correlation.

TABLE 4

Comparison of various measured values (Post-minus Pre-Treatment), Concentric Ring Scan eyes with high-risk age-related macular degeneration treated with panmacular SDM laser retinal protective therapy.

| Variable | Mean (SD) | Median (IQR) | p-value |
| --- | --- | --- | --- |
| M(d)/M(uv) Ratio, 24 Degree | 0.02 (0.21) | 0.01 (−0.09, 0.12) | 0.44 |
| M(d)/M(uv) Ratio, 16 Degree | 0.05 (0.22) | 0.07 (−0.10, 0.20) | 0.07 |
| M(d) Measure, 24 Degree | 0.04 (0.38) | 0.02 (−0.20, 0.23) | 0.52 |
| M(d) Measure, 16 Degree | 0.04 (0.26) | 0.03 (−0.13, 0.21) | 0.27 |
| M(uv) Measure, 24 Degree | 0.01 (0.36) | 0.00 (−0.18, 0.20) | 0.86 |
| M(uv) Measure, 16 Degree | −0.04 (0.36) | −0.03 (−0.21, 0.15) | 0.41 |

Table 4 shows the comparisons of interest for the PERG Concentric Ring Test dataset. Each row shows the difference (first post-treatment minus pre-treatment) in M(d)/M(uv) ratio, M(d) measure, or M(uv) measure, at the 24 and 16 degrees. In order to test whether the mean difference is different from zero, linear mixed models predicting the measure were performed, using an indicator for time as a covariate, also adjusting for left or right eye, and including a random patient intercept. The p-values are those associated with the time (pre-versus post-) regression coefficient. A significant p-value indicates that the mean difference is significantly different from zero. The table shows that all comparisons are not statistically significant. This method accounts for inter-eye correlation.

10/10 eyes with IRD improved by PERG following SDM. CR 16° testing was not improved (P=0.19), but CR 24° (MagD(uV)/Mag(uV) ratios (P=0.002) and MagD(uV) amplitudes (P=0.006) were both improved.

TABLE 5

Comparison of various measured values (Post-minus Pre- Treatment) eyes with heritable retinal disorders treated by panmacular SDM retinal protection.

| | All Eyes (N = 16) | | | Treated Eyes (N = 10) | | | Untreated Eyes (N = 6) | | |
|---|---|---|---|---|---|---|---|---|---|
| Variable | Mean (SD) | Median (IQR) | p-value[a] | Mean (SD) | Median (IQR) | p-value[a] | Mean (SD) | Median (IQR) | p-value[a] |
| M(d)/M(uv) Ratio, 24 Degree | 0.11 (0.21) | 0.07 (0.01, 0.22) | 0.04 | 0.21 (0.17) | 0.19 (0.08, 0.25) | 0.002 | −0.07 (0.13) | −0.03 (−0.23, 0.05) | 0.56 |
| M(d)/M(uv) Ratio, 16 Degree | 0.07 (0.18) | 0.06 (−0.01, 0.16) | 0.08 | 0.08 (0.22) | 0.07 (0.00, 0.33) | 0.19 | 0.06 (0.09) | 0.06 (−0.01, 0.14) | 0.22 |
| M(d) Measure, 24 Degree | 0.10 (0.22) | 0.12 (−0.04, 0.21) | 0.08 | 0.19 (0.20) | 0.17 (0.11, 0.24) | 0.006 | −0.05 (0.16) | −0.04 (−0.18, 0.04) | 0.44 |
| M(d) Measure, 16 Degree | 0.07 (0.19) | 0.06 (−0.01, 0.20) | 0.13 | 0.06 (0.22) | 0.06 (−0.02, 0.22) | 0.39 | 0.08 (0.15) | 0.06 (0.02, 0.18) | 0.22 |

SD = Standard Deviation, IQR = Interquartile Range
[a]Wilcoxon Signed Rank Sum Test Table 5 shows the comparisons of interest for the RP dataset. Each row shows the difference (post-minus pre-treatment) in M(d)/M(uv) ratio or M(d) measure, at the two degree options. Shown are the statistics for all eyes, treated eyes, and untreated eyes. Statistical significance was tested using Wilcoxon signed rank sum tests due to the small sample size and likely violation of the normality of these measures. The table shows that M(d)/M(uv) ratio, 24 degree is significantly higher post-treatment compared to pre-treatment in all eyes (p=0.04, positive values indicate higher post-treatment values, negative values indicate higher pre-treatment values) and in treated eyes (p=0.002). Also, we see that M(d) 24 degree is significantly higher post-treatment compared to pre-treatment in treated eyes (p=0.006). The other comparisons are not statistically significant.

In AMD, AMP average thresholds were improved following SDM (P=0.0439). CVA testing showed significant improvements in VA for all 6 levels of contrast, from 99% to 35%. (P values from P=0.049 to P=0.006).

TABLE 6

Summary of calculated difference (post-minus pre-treatment) for eyes with age-related and inherited retinal degenerations treated with panmacular SDM retinal protective therapy, Automated Microperimetry (AMP) eyes accounting for possible inter-eye correlation.

| Variable | Mean (SD) | Median (IQR) | p-value |
|---|---|---|---|
| Reduced Threshold ($N_{miss}$ = 8) | 2.72 (16.98) | 0.00 (−6.75, 6.75) | 0.8487 |
| Average Threshold | 11.12 (28.02) | 0.35 (−0.85, 2.65) | 0.0439 |
| P1 | −4.85 (33.30) | 0.50 (−12.00, 7.50) | 0.4664 |
| P2 | −0.08 (21.04) | 0.00 (−5.50, 5.00) | 0.9049 |

Table 6 shows the comparisons of interest for the AMP dataset. Each row shows the difference (follow up-minus pre-operation) in reduced and average threshold as well as P1 and P2. In order to test whether the mean difference is different from zero, a linear mixed models predicting the measure, using an indicator for time (pre-op versus follow-up) as a covariate, also adjusting for left or right eye, and including a random patient intercept was performed. The p-values are those associated with the time (pre-op versus follow-up) regression coefficient. A significant p-value indicates that the mean difference is significantly different from zero. Only average threshold is significantly different pre-op versus follow-up.

TABLE 7

Summary of calculated difference (post-minus pre-treatment), visual acuity on LogMAR scale measured by the Central Visual Acuity Analyzer in eyes with age-related and inherited retinal degeneration treated with panmacular SDM retinal protective therapy.

| Variable | N | Mean (SD) | Median (IQR) | p-value |
|---|---|---|---|---|
| 99% Contrast | 73 | −0.146 (0.511) | −0.073 (−0.336, 0.114) | 0.02 |
| 75% Contrast | 73 | −0.148 (0.488) | −0.058 (−0.301, 0.107) | 0.01 |
| 65% Contrast | 73 | −0.151 (0.458) | −0.109 (−0.301, 0.067) | 0.006 |
| 53% Contrast | 73 | −0.107 (0.444) | −0.032 (−0.248, 0.097) | 0.049 |
| 43% Contrast | 73 | −0.103 (0.370) | 0.000 (−0.250, 0.058) | 0.02 |
| 35% Contrast | 73 | −0.104 (0.416) | −0.044 (−0.248, 0.105) | 0.03 |

Table 7 shows the difference (post-minus pre-treatment) for each contrast level. In order to test whether the mean difference is different from zero, linear mixed models predicting the visual acuity, using an indicator for time as a covariate, also adjusting for left or right eye, and including a random patient intercept were used. The table shows significant improvement at all contrast levels. This method accounts for inter-eye correlation.

Linear regression analyses revealed significant negative correlations for all testing measures in both AMD and IRD, indicating that the worse the preoperative measure, the greater the likelihood of postoperative improvement.

28/33 eyes improved by PERG at one-month post SDM remained improved by PERG at 6-9 months post SDM. It is possible that other testing means and measures may be implemented to confirm the beneficial effects of the invention. For example, Raman Spectroscopy could be potentially used as a real-time treatment monitoring method. Other testing procedures, including hyperspectroscopy and reflectometry could possibly used as well.

Retinal protective therapy, in accordance with the present invention, followed by timely functionally-guided retreatment has the potential to slow disease progression and reduce complications and visual loss over time. For example, it has been found that the invention as a prophylaxis, panretinal SDM was found to reduce the rate of progression of severe non-proliferative to proliferative diabetic retinopathy from the expected 50% per year to just 8.5%.

Although several embodiments have been described in detail for purposes of illustration, various modifications may be made without departing from the scope and spirit of the invention. Accordingly, the invention is not to be limited, except as by the appended claims.

What is claimed is:

1. A therapeutic process for treating an eye to stop or delay the onset or symptoms of retinal diseases, comprising the steps of:
    determining that an eye has a risk for a retinal disease before detectable retinal imaging abnormalities;
    generating a laser light beam that creates sublethal photocoagulation in retinal tissue to provide preventative and protective treatment of the retinal tissue of the eye; and
    exposing at least a portion of retinal tissue, including at least a portion of the fovea, to the laser light beam without damaging the retinal or foveal tissue.

2. The process of claim 1, wherein the determining step includes the step of ascertaining that the patient is at risk for age-related macular degeneration.

3. The process of claim 1, wherein the determining step includes the step of conducting a test to establish that the patient has a risk for a retinal disease.

4. The process of claim 3, wherein the test comprises a retinal physiology test.

5. The process of claim 1, wherein the treated retina comprises the entire retina.

6. The process of claim 1, wherein the exposing step includes exposing the laser light beam to the entire retina and fovea.

7. The process of claim 1, including the step of periodically retreating the retina.

8. The process of claim 7, including the step of periodically monitoring visual and/or retinal function or condition of the patient to determine when the retina of the patient is to be retreated.

9. The process of claim 7, including the step of retreating the retina of the patient according to a set schedule.

10. The process of any of claims 1-9, wherein the generating step comprises the step of generating a subthreshold sublethal micropulse laser light beam having a wavelength greater than 532 nm and a duty cycle of less than 10%.

11. The process of claim 10, wherein the generated laser light beam has a pulse length of less than 500 milliseconds.

12. The process of claim 10, wherein the generated laser light beam has a duty cycle of approximately 5% or less.

13. The process of claim 10, wherein the generated laser light beam has an intensity of 100-590 watts per square centimeter.

14. The process of claim 10, wherein the generated laser light beam has a wavelength of 550 nm-1300 nm.

15. The process of claim 14, wherein the generated laser light beam has a wavelength of approximately 810 nm.

16. The process of any of claims 1-9, including the step of manipulating the laser light beam into a geometric object or pattern of simultaneously generated and spaced apart treatment laser light spots.

17. The process of claim 16, wherein the manipulating step comprises the step of creating a predetermined number of simultaneously generated laser light spots to completely and confluently cover a desired treatment area.

18. The process of claim 16, wherein the geometric object or pattern of laser light spots cover the entire retina.

19. The process of claim 16, including the step of controllably moving the geometric object or pattern of laser light spots to treat adjacent retinal tissue.

20. The process of claim 19, wherein the moving step includes the step of incrementally moving the laser light beam geometric object or pattern a sufficient distance from where the laser light beam geometric object or pattern was previously applied to the retina to preclude thermal tissue damage.

* * * * *